United States Patent [19]
DiBiasi et al.

[11] 4,412,961
[45] Nov. 1, 1983

[54] METHOD AND APPARATUS FOR MEASUREMENT AND CONTROL OF CELL SIZE IN A FOAM STRUCTURE

[75] Inventors: Daniel J. DiBiasi; Charles M. Krutchen, both of Pittsford, N.Y.

[73] Assignee: Mobil Oil Corporation, New York, N.Y.

[21] Appl. No.: 334,093

[22] Filed: Dec. 23, 1981

[51] Int. Cl.³ .............................................. B29D 27/00
[52] U.S. Cl. ...................................... 264/40.1; 264/53; 264/DIG. 13; 356/378; 356/391; 356/448; 425/140; 425/817 C
[58] Field of Search ....................... 264/40.1, 40.4, 53, 264/DIG. 13; 425/140, 817 C; 356/378, 391, 256, 446, 335, 448

[56] References Cited
U.S. PATENT DOCUMENTS

| | | | |
|---|---|---|---|
| 3,482,006 | 12/1969 | Carlson | 264/53 X |
| 3,511,571 | 5/1970 | Ogle | 356/391 X |
| 3,527,535 | 9/1970 | Monroe | 356/391 X |
| 3,953,739 | 4/1976 | Colombo et al. | 356/446 X |
| 4,329,052 | 5/1982 | Colombo et al. | 356/335 |

OTHER PUBLICATIONS

Fehn, Gregory M., "Extrusion Behavior of Cellular High-Density Polyethylene", In *Journal of Cellular Plastics*, Oct. 1967, pp. 456-462.
Bender, Rene J., "Handbook of Foamed Plastics," Libertyville, Ill., Lake Publishing Corp., ©1965, pp. 54, 55, 63-65, 79, 80, 84, 85.
Benning, Calvin J., "Plastic Foams: The Physics and Chemistry of Product Performance and Process Technology: vol. 1; Chemistry and Physics of Foam Formation," New York, Wiley-Interscience, ©1969, pp. 54-61, 71-82, 295-305, 343, 515.
Encyclopedia of Chem. Tech., Kirk-Othmer, 3rd Ed., vol. 20, p. 594.
Encyclopedia Americana, 1980, vol. 29, pp. 594-595.

*Primary Examiner*—Philip E. Anderson
*Attorney, Agent, or Firm*—Alexander J. McKillop; Michael G. Gilman; James P. O'Sullivan, Sr.

[57] ABSTRACT

A method and apparatus for monitoring the average cell size of a plastic foam structure continuously emerging from a production extrusion source which include means and process steps for magnifying an image of an area of a cross-section of said foam structure, developing said image and comparing the cell size of the image with a known standard and controlling production process parameters to obtain a foam structure of predetermined average cell size.

9 Claims, 1 Drawing Figure

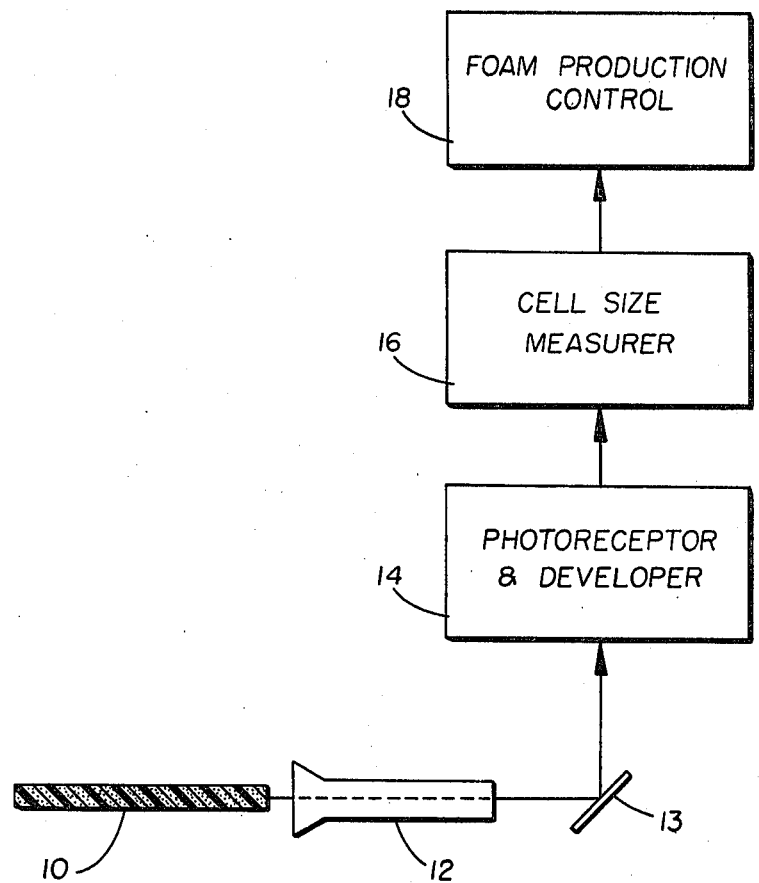

METHOD AND APPARATUS FOR MEASUREMENT AND CONTROL OF CELL SIZE IN A FOAM STRUCTURE

BACKGROUND OF THE INVENTION

The present invention relates to a method for monitoring and/or controlling the average cell size of a plastic foam structure continuously emerging from a production extrusion source. The invention also relates to an apparatus for monitoring and/or controlling the average cell size of such a foam structure.

By continuously monitoring this foam characteristic, i.e., cell size, the variation of which has a pronounced affect upon the physical properties of the foam, prompt processing and/or material feed (e.g., blowing agent, nucleating agent, etc.) adjustments may be made to bring the cell size back into a specified range in the event that it deviates therefrom.

It is known in the prior art that during the extrusion of polymer foam, cell size is the structural parameter which can be modified most readily and, furthermore, has a pronounced affect on the foam properties. These properties include compressive strength, tensile strength, elongation at break, tear strength and thermal insulating values. Cell size can be varied by orders of magnitude in a full scale production process by manipulating the necessary process parameters, nucleating agent, melt temperature, and so forth. The quantification of cell size is, under normal circumstances, tedious and time consuming. Normally a thin section of foam is prepared using a suitable cutting device, microtome, or its equivalent. The sample is then examined under a microscope or an image of the cell structure is projected onto a frosted glass plate in magnified form. An attempt is made to characterize the cell size by measuring the mean diameter of the cell or counting the number of cells contained in a given area. Obviously these prior art methods do not lend themselves to reproducible or standardized measurement. They do not necessarily reflect the average cell size of the same under investigation, since distribution of cell sizes occur in most foam polymer systems and single point measurements cannot always be translated into an average measurement. In addition, these kinds of cell size quantification can be costly in a production situation. Poor quality and/or "off-specification" material can be manufactured for long periods of time while an out-of-line cell size measurement is being made. Accordingly, it is an object of the present invention to provide a more accurate method and system for determining the cell size of polymeric foams. Further, the present invention provides an automatic process for determining and recording cell size substantially, continuously or at predetermined time intervals.

SUMMARY OF THE INVENTION

The present invention relates to a method for monitoring the average cell size of a plastic foam structure continuously emerging from a production extrusion source which comprises:

presenting a cross-section of an area of said structure to an optical projection means capable of projecting a magnified image of said area;

projecting a magnified image of said area through said means to a photoreceptor device to form thereon a latent image of said area;

developing said image to form a visible image of said area;

determining the average cell size of said area from said visible image; and in response to said size, controlling production process parameters to obtain a foam structure of predetermined average cell size.

The apparatus for controlling the average cell size of a plastic foam structure continuously emerging from a production extrusion source comprises:

means for presenting a cross-section of an area of said foam to an optical projection means capable of projecting a magnified image of said area;

photoreceptor means in association with said projection means for receiving a magnified latent image of said area;

means for developing said latent image in association with said photoreceptor means;

means for measuring the average cell size of a developed image of said area; and means responding to the measurement value to control process parameters to obtain a foam structure of predetermined cell size.

BRIEF DESCRIPTION OF THE DRAWING

The FIGURE is a schematic diagram of an apparatus which may be employed in the practice of the present invention.

DESCRIPTION OF SPECIFIC EMBODIMENTS

Techniques for the extrusion of polystyrene foam are well known in the art and a particularly desirable method is disclosed in U.S. Pat. No. 3,482,006, the disclosure of which is incorporated herein by reference. Generally, prior to extrusion, polystyrene pellets are coated with or admixed with a nucleating agent. Typical of such nucleating agents is a mixture of sodium bicarbonate and citric acid, although others may be employed. The nucleating agent which is admixed with the polystyrene serves to control the cell size of the cells contained in the extruded foam product. Following admixing of the nucleating agent with the polystyrene resin, the mixture is fed to a standard rotating screw-type extruder, wherein it is thoroughly mixed and melted as it is advanced towards the melted end of the extruder. A blowing agent such as pentane or isopentane is injected into the extruder downstream of the feed hopper. The pentane blowing agent is thoroughly admixed with a melted polystyrene and nucleating agent and this mixture is eventually extruded from the extrusion system through a die, either in the form of a flat, foam sheet or a tubular structure which is subsequently cooled, slit and the polystyrene foam sheeting recovered. As indicated above, it is of prime importance that the size of the individual cells of the foam structure be regulated within close tolerances. Cell size variation in a finished foam product has a pronounced affect on the properties of the foam structure. Although foam cell size may be controlled or rather varied by varying process parameters, the prime control means for adjusting foam cell size is usually by control of the concentration of nucleating agents in the extrusion system. This concentration, however, during continuous extrusion processes, may vary somewhat due to the vagaries of the system, such as, erratic feed at the nucleant feed hopper, incomplete or nonuniform mixture of the nucleants with the resin, and other undesirable conditions. It has now been found that irregularities in the average size of the cells in the extruded foam sheet may be monitored at will and quickly discovered and corrected by use of a developed and/or printed magnified image of a cross-section of an area of the foam structure taken of the in-line extruded product.

One form of apparatus that may be employed to practice the method of the present invention is schematically represented in the FIGURE. As shown therein, 10 is an edge view of a section of extruded polystyrene foam produced by the general process described above. In close proximity to a cross-section of foam sheet 10 is an optical projection means capable of projecting a magnified image of an area of said cross-section onto the photoreceptor of means 14 by way of any convenient device, such as mirror 13. The photoreceptor and developer means 14 can conveniently be a commercially available micro-fiche electrophotographic copier capable of developing a hard copy showing the polystyrene foam cells at approximately 90 to 100 times their actual size. The projection, magnification, photoreceptor and developer system can also be a commercially available laboratory camera of the "instant" photographic chemically developed photographic image type, equipped with a microscope magnification system. Such a camera is available from the Polaroid Corporation. The hard copy output from the photoreceptor and developing means 14 is transported to a cell size measurer 16. At this point the cell size as shown in the output of means 14 can be determined by comparing this output with a standard representing the acceptable cell size limits for the product desired. This comparison can be accomplished in cell size measured either automatically or by operator inspection visually. In the automatic version, a comparison in density between a photoreproduction of the magnified cells of a standard and the photoreproduction of the cells of the production material can be sensed or compared by means of a photocell. When it appears that the cell size is either too large or too small with respect to a particular cell size desired, this information is transmitted to foam production control means 18. This can be a commercially available sensing and response system for altering the production parameters in order to return the process conditions to that which will provide the desired cell size in the extruded sheet. Computer control can accomplish these process alterations. As indicated above, the principal change will be accomplished by an increase or decrease in the concentration of the nucleating agent being admixed with the resin prior to introduction of the mixture into the extruder system. As hereinbefore noted, it is also possible to vary other process parameters to obtain variation in cell size such as, for example, the density of the blowing agent concentration, melt temperature, etc.

EXAMPLE

A typical example of forming polystyrene sheet can be as follows; polystyrene resin pellets are admixed with the nucleating agent comprising sodium bicarbonate and anhydrous citric acid. The nucleating agent can constitute 0.58% by weight based upon the total weight of the polystyrene being charged. The acid to bicarbonate ratio can be 1:0.76. These materials are continuously fed into a feed hopper of, for example, a 2½ inch diameter screw extruder having a L/D ratio of 24:1. The extruder is operated at an extrusion rate of about 150 pounds per hour and the extrusion screw is internally cooled with water at a temperature of about 72° F. By means of extruder barrel heaters, the portion of the extruder barrrel surrounding the feed zone of the extruder is maintained at a temperature of about 220° F. In the melting zone, pentane injection zone, and the mixing zone, the extruder barrel is maintained at a temperature of from about 400° F. to 450° F. A liquid pentane blowing agent is injected through the extruder barrel, about 5% by weight of pentane based upon the total weight of resin and nucleating agent, and into the polystyrene composition at a point beyond the feed section where the polystyrene is in a molten condition. The molten mass is then passed through the extruder mixing zone and finally through the cooling section of the extrusion system before being extruded through an annular die orifice, affixed to the terminal end of the extruder. The extruded foam in tubular form is slit open to a flat sheet and an edge cross-section is presented to the apparatus hereinabove described and shown in the FIGURE. The average size of the foam cells in the foam sample is then measured as indicated above.

The hard copy of the magnified sample can be a xerographic print-out or a Polaroid positive print. In both cases, in addition to revealing the nature and size of the cells in relation to a known standard a permanent record is available for this particular production run taken at a particular time in the production run.

The images of the cross-section of the foam can be taken at any convenient time interval, for example in sequences of seconds, minutes or hours.

Proper focus of the cell area to be enlarged and reproduced can be accomplished by any of several photographic techniques known to one skilled in the art. For example, the moving extruded foam film can be momentarily tracked or scanned by the copying system, or the foam film can be momentarily retarded to accommodate the speed of the copying system, or the speed of the copying system, particularly the Polaroid system, can be fast enough to accomplish the sharply focused exposure without these accommodations.

While the present invention has been described with respect to the monitoring of a polystyrene foam structure, it is to be understood that the method and apparatus employed herein is equally applicable to the monitoring of any plastic foam structure.

Although the present invention has been described with preferred embodiments, it is to be understood that modifications and variations may be resorted to without departing from the spirit and scope of this invention, as those skilled in the art will readily understand. Such variations and modifications are considered to be within the purview and scope of the appended claims.

What is claimed is:

1. A method for monitoring the average cell size of a plastic foam structure continuously emerging from a production extrusion source which comprises:

presenting a cross-section of an area of said structure of the in-line extruded product to an optical projection means capable of projecting a magnified image of said area;

projecting a magnified image of said area through said means to a photoreceptor device to form thereon a latent image of said area;

developing said image to form a visible image of said area;

determining the average cell size of said area from said visible image by comparison with a known standard representing exceptable cell size limits; and in response to said size, controlling process parameters to obtain a foam structure at least generally corresponding to said known standard.

2. The method of claim 1 wherein said images are taken and developed at any time intervals.

3. The method of claim 1 wherein said visible image is a xerographic image.

4. The process of claim 1 wherein said visible image is a chemically developed photographic image.

5. The method of claim 1 wherein said production process parameters are automatically controlled in response to the determined average cell size of said area.

6. An apparatus for controlling the average cell size size of a plastic foam structure continuously emerging from a production extrusion source which comprises:

an optical projector capable of projecting a magnified image of an area of a cross-section of said foam structure of the in-line extruded product;

means for moving a cross-section of said foam structure past said projector;

photoreceptor means in association with said projector and capable of receiving a magnified latent image of said area;

developer means in association with said photoreceptor means capabale of developing said latent image;

measuring means in association with a developed image of said photoreceptor for measuring the average cell size of said area by comparison with a known standard representing exceptable cell size limits; and control means in association with said measuring means responsive to measurement values to control production process parameters to obtain a foam structure at least generally corresponding to said known standard.

7. The apparatus of claim 6 wherein said photoreceptor means and developing means are part of an electrophotographic system.

8. The apparatus of claim 6 wherein said photoreceptor means and developing means are part of an instant chemical development photographic system.

9. The apparatus of claim 6 wherein said means responding to the measurement value is an automatic means.

* * * * *